United States Patent
Scharlack et al.

(10) Patent No.: US 6,925,198 B2
(45) Date of Patent: Aug. 2, 2005

(54) METHOD AND SYSTEM FOR THREE-DIMENSIONAL MODELING OF OBJECT FIELDS

(76) Inventors: Ronald S. Scharlack, 121 Colbourne Crescent, Brookline, MA (US) 02445; Bethany F. Grant, 655 First Parish Rd., Scituate, MA (US) 02066-3106

(*) Notice: Subject to any disclaimer, the term of this patent is extended or adjusted under 35 U.S.C. 154(b) by 0 days.

(21) Appl. No.: 10/154,717

(22) Filed: May 24, 2002

(65) Prior Publication Data

US 2003/0219148 A1 Nov. 27, 2003

(51) Int. Cl.[7] ............................................. G06T 17/00
(52) U.S. Cl. ......................................... 382/128; 382/154
(58) Field of Search ................................. 382/154, 128; 433/215, 229

(56) References Cited

U.S. PATENT DOCUMENTS

| | | | | |
|---|---|---|---|---|
| 4,859,181 A | * | 8/1989 | Neumeyer .................... 433/69 |
| 5,237,998 A | * | 8/1993 | Duret et al. ................. 128/665 |
| 5,598,515 A | | 1/1997 | Shashua ...................... 395/122 |
| 5,642,293 A | * | 6/1997 | Manthey et al. ............. 364/508 |
| 5,851,115 A | | 12/1998 | Carlsson et al. ............. 433/215 |
| 5,857,853 A | | 1/1999 | van Nifterick et al. ..... 433/213 |
| 6,108,497 A | * | 8/2000 | Nakayama et al. .......... 396/429 |
| 6,405,071 B1 | * | 6/2002 | Analoui ....................... 600/425 |
| 2002/0028418 A1 | * | 3/2002 | Farag et al. .................. 433/29 |
| 2003/0012423 A1 | * | 1/2003 | Boland et al. ............... 382/154 |

* cited by examiner

*Primary Examiner*—Brian Werner
(74) *Attorney, Agent, or Firm*—Philip G. Koenig

(57) ABSTRACT

A method and system for creating three-dimensional models of implant-bearing dental arches, and other anatomical fields of view, employs three-dimensional scanning means to capture images of an anatomical field of view wherein there have been positioned (and preferably affixed to an anatomical feature) one or more three-dimensional recognition objects having a known geometry, such as a pyramid or a linked grouping of spheres. Image processing software is employed to locate and orient said recognition objects as reference data for stitching multiple images and thereby reconstructing the scanned field of view. Recognition objects placed in areas of low feature definition enhance the accuracy of three-dimensional modeling of such areas.

15 Claims, 4 Drawing Sheets

METHOD AND SYSTEM FOR THREE-DIMENSIONAL MODELING OF OBJECT FIELDS

FIELD OF THE INVENTION

The invention is a method and system for determining the relative location of objects and features in a plurality of overlapping scanned images. The invention is particularly directed to medical and dental applications including those that require surgical and prosthetic devices to be designed and manufactured to precise dimensions dictated by the anatomy of individual patients.

BACKGROUND OF THE INVENTION

Many surgical procedures concern the temporary or permanent insertion, into the soft or bony tissue of a patient, of prosthetic and other artificial devices that are required to fit the anatomy of the patient to a very high degree of precision and accuracy. One such application concerns implant dentistry, in the course of which one or more (usually metallic) implant anchors are surgically placed within the jawbone of a patient, to receive and support prosthetic components designed to simulate and replace one or more natural teeth lost by the patient. It is well known that, to be wholly successful, implant procedures must adhere to very strict placement, orientation and sizing requirements determined by existing bone structure and dentition, whereby the prosthetic components to be fitted onto surgically-placed implant anchors must preferably be designed, shaped and sized specifically to conform to the precise anatomical geometry of the patient, including the location, shape and size of adjoining teeth, and must transition to the precise orientation of the principal axis of the supporting implant anchor with a high degree of accuracy.

Conventional methods for meeting these rigorous requirements provide for the creation of a model of the patient's jaw and dentition, the making of said model comprising the taking of a so-called "impression" of the patient's dentition, using a malleable substance placed over and around the teeth in the patient's mouth comprising the entire dental arch. Typically this impression is taken following the surgical insertion of the implant anchors. Typically, reference components called impression copings are affixed to the external extremity of the inserted implant anchors, and serve to reference the location and angular orientation of the anchors. Subsequently, a model made from a mold based on said impression will incorporate so-called "analog" anchors to model the anchors in the patient's jaw, and prosthetic devices for said anchors will be designed and manufactured based on the geometry of the model created as described.

In actual practice the conventional procedure described above is fraught with numerous difficulties and shortcomings. It has proven impossible for dental practitioners to make dental impressions, and thus models, that are consistently free of dimensional and positional errors; so rigorous are the geometrical requirements involved in such applications that even a sub-millimeter dimensioning error, or a 1 or 2 degree orientation error, will result in prosthetic placements that give rise to unacceptable stresses and conditions.

In recent years efforts have been made to employ image-based modeling techniques to address these well-known problems of conventional implant dentistry procedures. In these efforts, images are taken of the patient's mouth, and a three-dimensional model of the pertinent regions is recreated using so-called three-dimensional image processing techniques and software. The field of photogrammetry, which traces its origins to the decade following the invention of photography in the 1830s, is "the art, science and technology of obtaining reliable information about physical objects and the environment through the processes of recording, measuring, and interpreting photographic images and patterns of electromagnetic radiant energy and other phenomena." (Manual of Photogrammetry, American Society of Photogrammetry and Remote Sensing, $4^{th}$ Ed., 1980). Particularly with the advent of computers having fast processing speeds and large memories, and the advent of low-cost digital cameras and other image-capture devices, off-the-shelf three-dimensional image processing software has become readily available that is applicable to a wide variety of virtual modeling applications. Using such software, it has become possible to reconstruct reasonably accurate three-dimensional models of an imaged subject field using available commercial products. However the particular demands for great accuracy, and the physical strictures of imaging the human body, have thus far resulted in the absence, in the field of dentistry, of acceptable three-dimensional imaging techniques. A particular problem is the necessity, for the accurate reconstruction, in the form of a virtual model, of an imaged scene, that the scene be imaged from at least two positions, thereby providing the geometric data required for the application of triangulation methods by the software.

U.S. Pat. No. 5,851,115 issued Dec. 22, 1998 to Carlsson, et al, describes a photogrammetric method and system for imaging the mouth, for the purpose of creating a virtual model of the patient's mouth from which dental parts may be designed and made. In the system according to Carlsson et al a specialized camera is employed, comprising a set of mirrors that enable a single exposure to embody stereographic images from two different angles. The system of Carlsson further requires that the relative geometry of the virtual "lenses" created by the mirror system be known precisely. To assist the software in locating and orienting imaged features, Carlsson teaches the use of reference markings, such as circles, applied to flat surfaces within the imaged field.

U.S. Pat. No. 5,857,853 issued Jan. 12, 1999 to van Nifteric et al. also discloses a photogrammetry-based method for capturing the dimensional and orientation data required for the manufacture of dental prosthetic parts used in implant dentistry. In order to obtain the at-least-two views required by the triangulation engine of the photogrammetry software, the method of van Nifteric et al employs either a plurality of cameras having precisely-known relative positions, or a single camera mounted on a swiveling carriage that is movable between separated but accurately defined positions. van Nifteric et al. further teach the use of recognition objects and points, to serve as reference points used by the photogrammetry software in positioning features of the imaged scene within a coordinate frame. van Nifteric et al. thus disclose the use of a bar comprising measuring scale markings, and of two spheres mounted on a pin, as recognition objects.

While the methods disclosed in the Carlsson et al. and van Nefteric et al. patents constitute significant advances, these methods still exhibit several important disadvantages and shortcomings that render them impractical for most implant dentistry practitioners. Both of said methods require the use of highly specialized and accordingly expensive camera equipment, and both require that such camera equipment be precisely aligned, to capture a plurality of images from precisely known relative lens positions. Functionally, both methods are inadequate to image accurately a wide field of view, particularly a wide field of view comprising areas characterized by very low feature definition, a condition typical of the edentulous (tooth-free) jaw and thus quite common in implant dentistry practice. The present invention addresses these shortcomings of the prior art, and it provides a three-dimensional-based virtual modeling method, specifically directed to medical and dental applications, that is remarkably low cost and that provides improved feature reconstruction accuracy particularly in applications that require the use of several combined images.

SUMMARY OF THE INVENTION

The present invention is a three-dimensional-based modeling method designed for dentistry and related medical applications. One aspect of the invention dispenses with the need for a specific camera and instead enables the use of any data capture means that produces a point cloud representing the three dimensional surface. Such data capture means may for example be a hand-held or frame-fixed three-dimensional laser scanner, an ordinary digital camera, or any other imaging means that is practically suited to the particular medical application. Another aspect of the invention is the use of three-dimensional recognition objects, to assist photogrammetry software to locate automatically, and to determine accurately the position and orientation of objects within the image field. Yet another aspect of the invention is the positioning of recognition objects having well-defined topography within those areas in the image field that have low image definition, and particularly in such of these areas that appear in overlapping portions of at least two images, to provide the photogrammetry software with position, angulation, and orientation information sufficient to enable highly accurate combining (or "stitching") of adjoining and overlapping images.

In the method of the invention, recognition objects having a known three-dimensional geometry that comprises well defined features disposed at accurately known relative positions, are fixedly positioned within the image field, and particularly in areas within the image field that have low feature definition. Examples of recognition objects include an object comprising three linked spheres having precisely known radii, fixed at precisely known positions on angled posts, as well as polygons of known dimensions such as pyramids. The image field is then scanned, such scanning effectively "panning" the image field to cover said image field in its entirety. Three-dimensional image processing software, preferably comprising algorithms set forth in this specification, is then employed to interpret the image data acquired by the scanning means and to determine a virtual three dimensional model that reconstructs, to a high degree of accuracy, the geometry of the scanned image field.

DESCRIPTION OF PREFERRED EMBODIMENTS OF THE INVENTION

The present invention is a method and system for creating virtual three-dimensional models of a scanned field of view, using three-dimensional recognition objects as reference points in the "stitching" of overlapping captured images, and, additionally, positioning such recognition objects in areas of the field of view that are characterized by low feature definition in order to enhance the accuracy of the three-dimensional modeling of such areas.

The invention is particularly suitable and intended for medical and dental applications, and it is particularly suited for use in the field of implant dentistry and related applications. Dental implants are used to support the restoration of missing teeth. Implant fixtures are surgically implanted by a dentist. These dental implants typically will be "restored" with abutments and crowns; that is, following successful implantation of implant fixtures into the jaw of the patient, complementary components including abutments and crowns will be affixed to the implanted fixtures to provide the patient with a restoration of the patient's natural teeth.

In an important aspect, the method and system of the present invention enable a manufacturer of dental restoration components to accurately measure the location and orientation of the implants in relation to the surrounding oral environment, and thereby to design and to machine restoration components that are, to a very high degree of precision and accuracy, customized to the anatomy and the existing dentition of the patient.

In applications directed to dentistry, and related medical applications, the present invention dispenses with the need for specialized camera and camera mountings. Instead the invention enables the use of any data capture means that produces a point cloud representing the three dimensional surface. Such data capture means may for example be a hand-held or frame-fixed three-dimensional laser scanner, an ordinary digital camera, or any other imaging means that is practically suited to the particular medical application. Image-data capturing means usable with the invention are readily available from commercial sources, and would for example include three-dimensional laser scanners, such as the VIVID 900 model scanner marketed by the Minolta Corporation.

Figure 6:
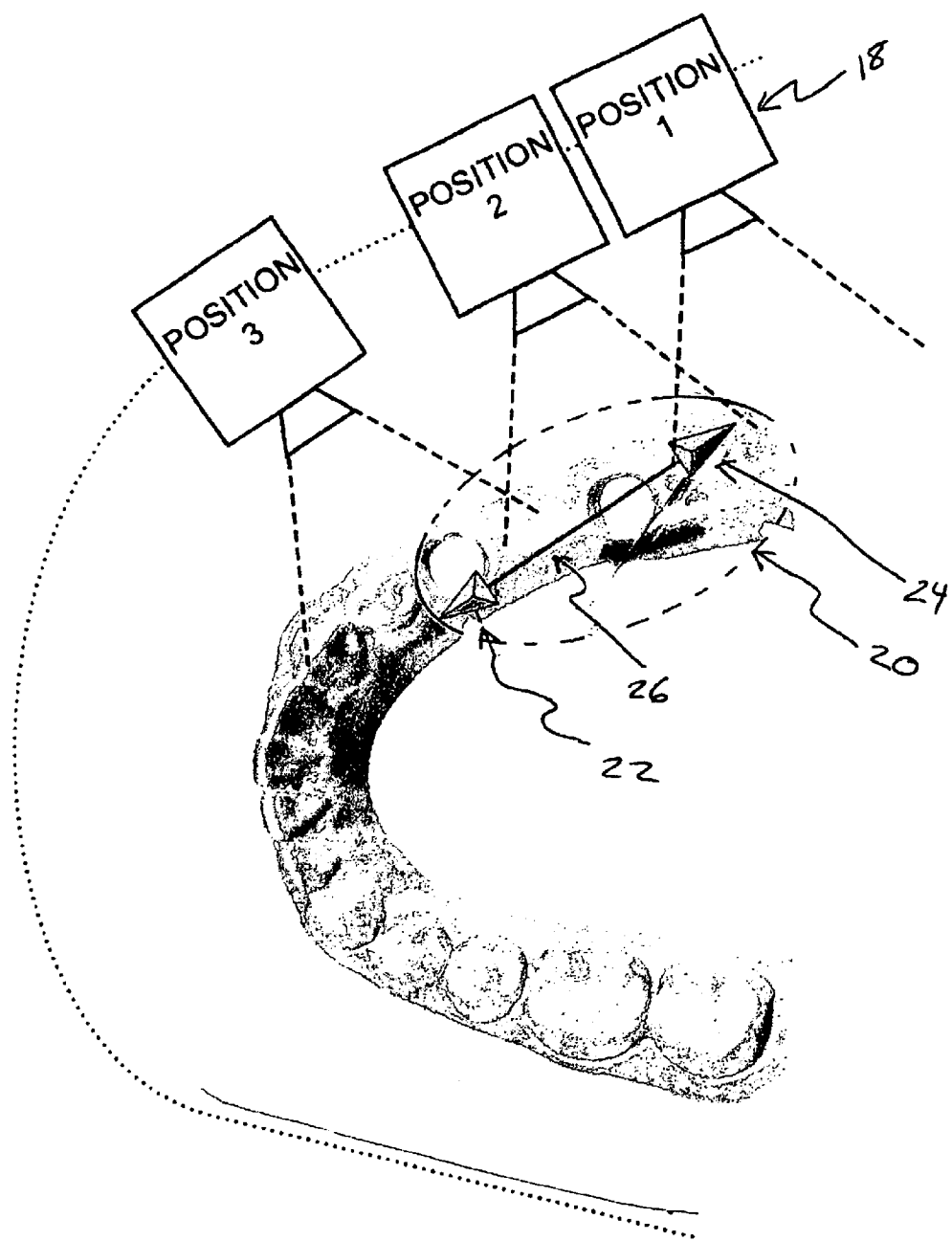
FIG. 6 Diagram illustrating an imaging operation according to the invention, comprising a perspective view of a dental arch with an edentulous "low definition" zone and including a fifth recognition object.

An important aspect of the invention is the use of three-dimensional recognition objects, illustrated in FIGS. 1–6, to assist photogrammetry software to locate automatically, and to determine accurately the position and orientation of objects within the image field. Yet another aspect of the invention is the positioning of recognition objects having well-defined topography within those areas in the image field that have low image definition, and particularly in such of these areas that appear in overlapping portions of at least two images, as illustrated in FIG. 6 to provide the imaging software with position and orientation information sufficient to enable highly accurate combining (or "stitching") of adjoining and overlapping images. The presence of such areas of low feature definition is typical of edentulous dental conditions, and thus presents a chronic problem to the imaging of edentulous jaws, which the present invention is the first to address successfully.

Figure 1:
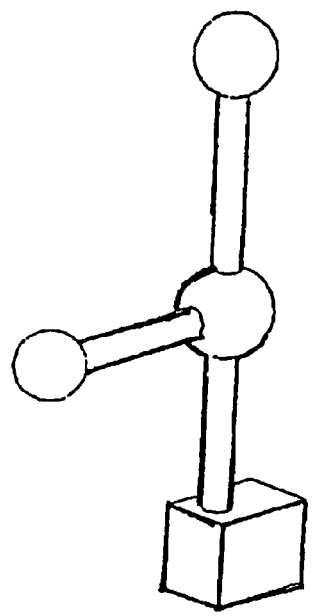
FIG. 1 Perspective view of a first recognition object according to the invention.
Figure 3:
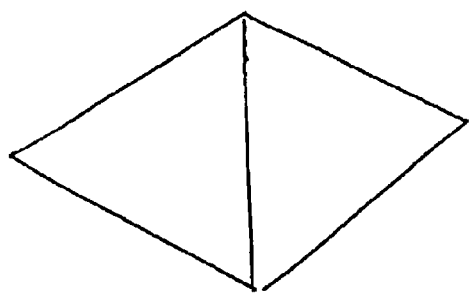
FIG. 3 Perspective view of a third recognition object according to the invention.

In the method of the invention, recognition objects having a known three-dimensional geometry that comprises well defined features disposed at accurately known relative positions, are fixedly positioned within the image field, and particularly in areas within the image field that have low feature definition. The preferred embodiments of recognition objects for use with the invention include an object, as illustrated in FIG. 1, that comprises three linked spheres having precisely known radii, fixed at precisely known positions on angled posts. Another preferred form of recognition object is shown in FIG. 3 and is a pyramidal polygon of known dimensions.

Figure 7:
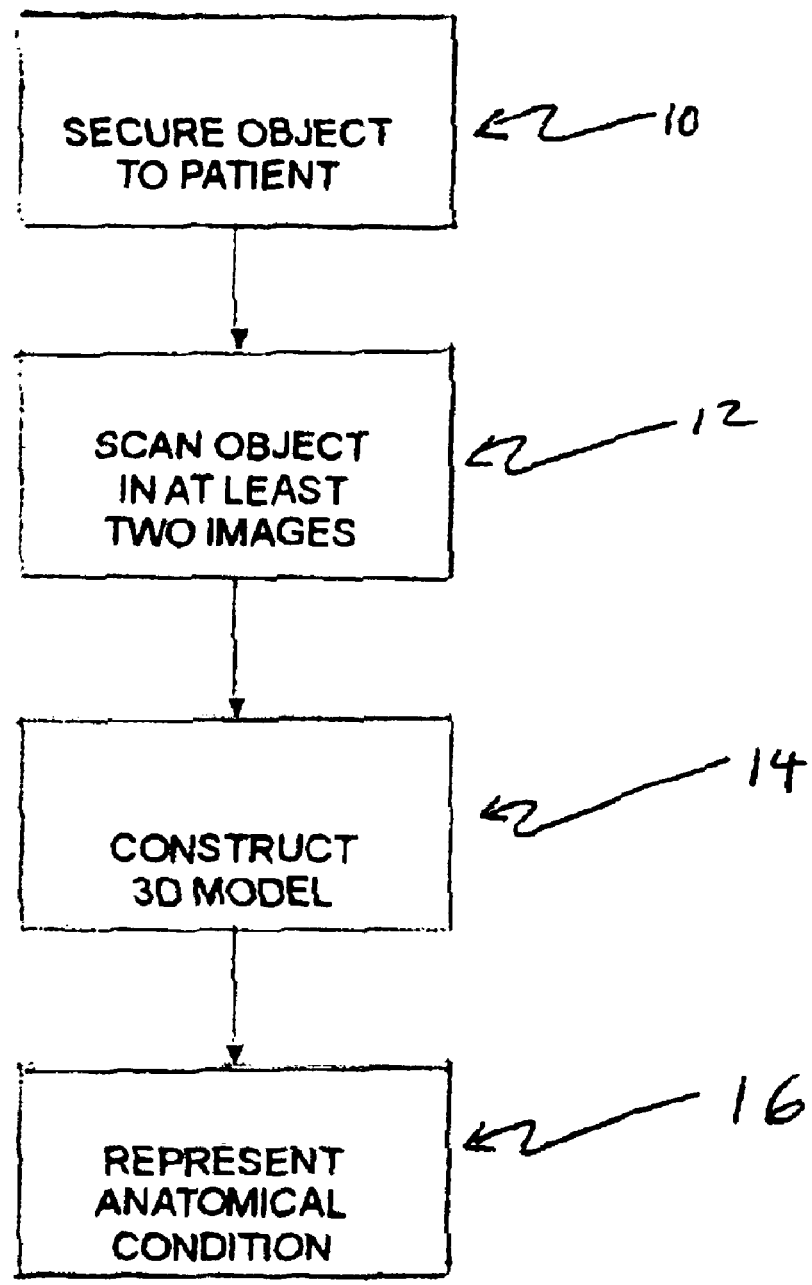
FIG. 7 Flowchart of a method according to the invention.

In the practice of the method of the invention, set forth in the flowchart of FIG. 7, recognition objects as shown in recognition objects as shown in FIGS. 1–6 are positioned within the image field, preferably by securing such recognition objects to objects within the field of view (step 10 in FIG. 7). In the case of implant dentistry the preferred method is to secure one or more recognition objects to dental implants that have been surgically implanted into the jaw of the patient. Preferably the selected recognition objects each comprise an attachment feature that is complimentary to the interface features of the dental implant. The recognition objects can be secured with a fastener having a threaded shaft insertable within a bore of the recognition object that may be oriented along the principal axis of the implant fixture.

The field of view is then scanned (step 12 in FIG. 7), using any suitable scanning means capable of capturing a cloud of data points representing features of the imaged field. Such scanning typically requires the taking of a plurality of overlapping images that collectively span the image field to cover said image field in its entirety, as diagrammed in FIG. 6, which illustrates scans taken by scanning means 18 in three positions. Various methods are currently employed at the time of scanning to recreate the entire model from these separate images. One such method uses precise information about the location of the model with respect to the camera to position and orient the multiple images. In addition, commercially available three-dimensional image processing software products also provide tools to combine discrete scans into a single model by matching the overlapping regions of the images. Well-known examples of suitable image-processing software include the Studio software marketed by Raindrop Geomagic, Inc.

The invention comprises a method and system for developing a virtual three-dimensional model of a dental restoration field. In one aspect the invention provides means for determining the relative location of recognition objects, and of features of recognition objects, in one or a plurality of scanned images obtained with a three-dimensional scanning means, and for detecting the location and the orientation of a known feature in a three-dimensional scanned object.

While the recognition object could be an intrinsic feature of an original object (or set of objects), preferably the recognition object is an artifact which is added to the original object field and which has a precisely known geometry. Using information about the geometry of the recognition object, software for use with the present invention enables the precise position and orientation of the recognition object to be identified with respect to the scanned data. Furthermore, multiple scans can be "registered" and their relative position and/or orientation precisely aligned, without any human intervention.

The field of view to be scanned must therefore comprise at least one object having features of known geometry, said features being sufficient to completely define location and/or orientation. Examples of these types of objects are shown in FIGS. 1–6. In a preferred embodiment of the invention the location object is scanned using a three-dimensional scanner, and the scanned data is typically collected as unordered ASCII text format; however any collection of three-dimensional point data is applicable.

From the scanned data the recognition object is detected by the imaging software, and the determination of its position and orientation (using its known geometry) enables also the determination of the position and orientation of all other objects and features captured in the scanned data.

This process of constructing a virtual 3D model of the imaged field of view (step 14 in the flowchart of FIG. 7) can be rapidly executed in a fully automated process employing efficient computer code. For example, in the example of three spheres used to define position and orientation (see FIG. 1), the centers of the three linked spheres (of known diameter and known distance from each other) are detected by the software. An origin is then calculated using the geometric relationship, and the location of the origin is typically output as a data point triple (x,y,z). The software may also calculate the orientation of the recognition object as two unit vectors, also expressed as data point triples. Similar methods are employed to determine the position and orientation defined by other objects of known geometry within the subject field, such as the spherical, polygonal, cylindrical and other shapes shown in FIGS. 1–6. In this way a set of data is obtained that fully defines the position and orientation of each recognition object.

Detecting an object of known geometry in a 3-dimensional scan has many potential applications. The medical and dental applications to which the present invention is principally directed involve a combination of organic surfaces and manufactured objects, and, in these applications, the ability to detect, to a high degree of accuracy, the position and orientation of an object of known geometry which is positioned within an anatomical field of view occasions the ability to design component parts that are customized to the topography of this anatomical field of view.

Figure 2:
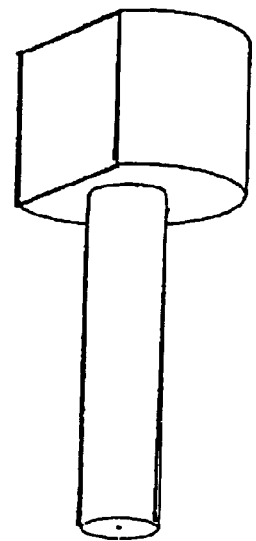
FIG. 2 Perspective view of a second recognition object according to the invention.

Specifically in the case of dental implants, for example, by mounting one of the recognition objects shown in FIGS. 1–3 onto the existing manufactured part (i.e. the implant itself), the exact location and orientation of this part within the dental arch of the patient can be determined; in turn this determination permits a virtual assembly to be made (in step 16 of the flowchart of FIG. 7) that combines the scanned image and proposed replacement and supplemental part (i.e. a replacement tooth), in order to select, and then manufacture, replacement and supplemental parts that exactly complement the geometrical requirements of the patient's anatomical conditions.

When multiple three-dimensional images of an object are taken (e.g. due to size or obscured views), it is necessary to define the relative location and orientation of each of the images in order to re-align the captured image data into a complete and accurate representation of the original field of view. In order to do this, there must be captured, in each image in the set of images, a recognition object of known geometry (such as those shown in FIGS. 1–6), which also appears in a second image in the set. The location and/or orientation of the known object in each image can then be used to position the images with respect to each other in order to recreate the original field of view.

This method can also be employed in conjunction with and to supplement currently practiced "stitching" or "registration" methods. These methods align multiple scans without the use of known geometry, but are insufficiently accurate for many applications. The addition to the field of view of one or more recognition objects according to the invention, as illustrated in FIGS. 1–6, greatly enhances the accuracy of the stitching of adjoining images. Furthermore the positioning of such recognition objects within any areas of the field of view that are characterized by low feature definition (e.g., area 20 in FIG. 6) will greatly enhance the three-dimensional modeling of such areas, in addition to serving as relative reference points between adjoining images that each comprise a given recognition object.

Figure 4:
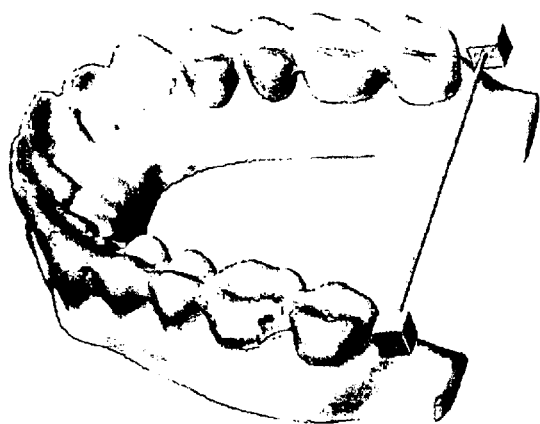
FIG. 4 Perspective view of a dental arch comprising a third recognition object.
Figure 5:
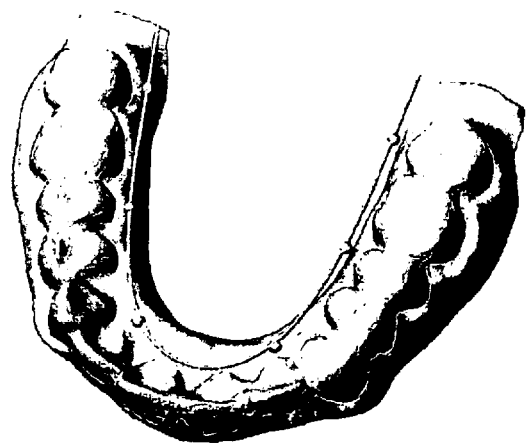
FIG. 5 Perspective view of a dental arch comprising a fourth recognition object.

By using physically connected, known geometric features as recognition objects in individual, overlapping images that collectively cover the field of view of interest, the relative position and orientation of these images can thus be determined. This aspect of the invention serves to eliminate sources of inaccuracy resulting from the known "stitching" methods that result in drift, warp and/or other distortions as scans are aligned. FIGS. 4 and 6 illustrate examples of this solution: in these case a dental arch is to be scanned. The known geometry introduced into the scan, in the form of two polygons of known dimensions, linked by a bar also having a known dimension, enables detection of location and/or orientation of scans of portions of the teeth. Intra-oral scanning necessitates the use of small scanners, such that each scan enables the capture of only a portion of the arch.

In the practice of the invention, spatial information may be obtained directly using intra-oral scanning and then processed as described above. In the alternative, however, the present invention may be used in conjunction with the conventional practice whereby impressions are taken of the patient's dentition, and said dentition is replicated in the form of a master cast made from said impressions. In an implant case, the master cast will contain analogs of the dental implants. The accuracy with which the locations and orientations of these implant analogs can be determined, for the purpose of designing restoration component parts to be supported by the implants, is enhanced by using a recognition object according to the present invention.

A preferred recognition object, also for use when imaging a master cast of a patient's dentition, is the object shown in FIG. 1, which consists of three spheres sized and positioned to unambiguously define position and orientation. Following the securing of such a recognition object to an implant analog within a master cast, the cast is scanned to produce a data file of space-coordinate points of the surface. Then, imaging software comprising a feature location algorithm serves to deduce the defining surfaces of the recognition objects within the scanned image (in this case the spheres), and thus derives the locations and the precise orientation of the implants, which it reports to the system's users. A second preferred recognition object, also for use in imaging a master cast of a patient's dentition, is a pyramid of known geometry, for example the isosceles base pyramids 22 and 24 linked by bar 26 as depicted in FIG. 6.

We claim:

1. A method, suitable for use in medical, dental and veterinary applications, for developing a virtual three-dimensional model of a therapeutic field of view, said method comprising:
   (a) securing, to an edentulous portion of a dental arch of a patient, at least one three-dimensional recognition object having a defined topography of precisely known dimensions that permits the determination of position and orientation of at least two images with respect to each other;
   (b) employing freely movable scanning means to capture visual images of said field of view, wherein the same recognition object appears in at least two captured images;
   (c) employing imaging software to develop a digitized construction, from said at least two of said images, of a virtual three-dimensional model of a portion of said field of view; and
   (d) employing said construction of a model of a portion of said field of view as base data to represent the anatomical condition of said patient.

2. The method according to claim 1, wherein at least one of said recognition objects comprises three spheres that have radii of known dimensions and that are affixed to angled posts, whereby the centers of said spheres form a triangle having precisely known dimensions.

3. The method according to claim 1, wherein at least one of said recognition objects comprises a pyramid having known dimensions.

4. The method of claim 3 wherein at least one recognition object comprises a pyramid that has a triangular base in the form of an isosceles triangle.

5. The method according to claim 3, wherein at least one of said pyramids is stepped.

6. A virtual modeling system for use in therapeutic medical, dental and veterinary applications, said system comprising:
   (a) at least one three-dimensional recognition object that has a defined topography of precisely known dimensions that permits the determination of position and orientation of at least two images with respect to each other, said recognition object being adapted to be secured to an edentulous portion of a dental arch of a patient;
   (b) freely movable scanning means adapted to capture visual images of a field of view comprising at least one said recognition object that has been secured to an anatomical feature of a patient;
   (c) imaging software adapted to develop a digitized construction, from at least two images of a field of view comprising a said recognition object, of a virtual three-dimensional model of said field of view.

7. The system of claim 6, comprising at least one recognition object that comprises three spheres that have radii of known dimensions and that are affixed to angled pins whereby the centers of said spheres form a triangle having precisely known dimensions.

8. The system of claim 6 comprising at least one recognition object that comprises at least one polygon having known dimensions.

9. The system of claim 8 comprising at least one recognition object that comprises at least two polygons that have known dimensions and that are joined by linking means having a known dimension.

10. The system of claim 8 comprising at least one polygonal recognition object having a pyramidal shape of known dimensions.

11. The system of claim 10 comprising at least one recognition object having a pyramidal shape and a triangular base in the form of an isosceles triangle.

12. The system according to claim 10, wherein at least one of said pyramids is stepped.

13. The system of claim 6 comprising recognition objects including three pyramids having known dimensions.

14. The system of claim 13 wherein said at least three pyramids are linked by means having known dimensions.

15. The system according to claim 6 wherein said recognition object comprises a geometrical feature in the shape of a solid cylinder from which a portion parallel to the main axis of the cylinder has been sliced off.

* * * * *